(12) United States Patent
Grindstaff (10) Patent No.: US 12,220,265 B2
(45) Date of Patent: Feb. 11, 2025

(54) BIOLOGICAL CONTAINMENT AND TRANSPORT CARRIERS AND METHODS THEREOF

(71) Applicant: Rex Grindstaff, Knoxville, TN (US)

(72) Inventor: Rex Grindstaff, Knoxville, TN (US)

(*) Notice: Subject to any disclaimer, the term of this patent is extended or adjusted under 35 U.S.C. 154(b) by 0 days.

(21) Appl. No.: 18/190,190

(22) Filed: Mar. 27, 2023

(65) Prior Publication Data

US 2023/0293256 A1  Sep. 21, 2023

Related U.S. Application Data

(63) Continuation of application No. 17/136,692, filed on Dec. 29, 2020, now abandoned, which is a
(Continued)

(51) Int. Cl.
*A61B 46/00* (2016.01)
*A61B 50/15* (2016.01)
(Continued)

(52) U.S. Cl.
CPC .............. *A61B 50/36* (2016.02); *A61B 46/00* (2016.02); *A61B 50/15* (2016.02); *A61B 50/31* (2016.02);
(Continued)

(58) Field of Classification Search
CPC ... A61B 2050/314; A61B 50/31; A61B 50/33; A61B 50/34; A61B 50/36; A61B 50/37;
(Continued)

(56) References Cited

U.S. PATENT DOCUMENTS

| 546,168 A | 9/1895 | Lobdell |
| 3,954,174 A | 5/1976 | Kraus |

(Continued)

FOREIGN PATENT DOCUMENTS

GB           247665         7/2011

*Primary Examiner* — Adam Baker
(74) *Attorney, Agent, or Firm* — Robinson IP Law, PLLC (57) ABSTRACT

A biological containment and transport carrier apparatus for use with an equipment table in an operating room, including a base layer having an inner surface and an opposing outer surface, a top layer having an inner surface and an opposing outer surface, a perimeter of the top layer being coupled to a perimeter of the base layer to form a sealed bag, an inner seam portion formed between the base layer and the top layer, the inner seam portion having a length and width dimension configured to respectively match a length and a width dimension of a top surface of an equipment table in an operating room, and a zipper formed within the top layer to open and close an insertion flap of the top layer so as to provide access to the inner seam portion such that when the zipper is open, at least a portion of the inner seam portion is configured to fold inside out over a top surface of the table and wrap around one or more outer edges of the table and extend a predetermined distance below the bottom surface of the table to secure the base layer to the table and to provide a sterile margin, or drape portion, around the table, and to provide a custom fit for the table to allow for sterile use in procedure of setup packs with reduced exposure of contaminated surfaces.

9 Claims, 7 Drawing Sheets

Related U.S. Application Data continuation of application No. 15/017,108, filed on Feb. 5, 2016, now abandoned.

(60) Provisional application No. 62/150,739, filed on Apr. 21, 2015.

(51) Int. Cl.
  A61B 50/31 (2016.01)
  A61B 50/33 (2016.01)
  A61B 50/36 (2016.01)
  A61B 50/00 (2016.01)
  A61B 50/30 (2016.01)

(52) U.S. Cl.
  CPC ...... A61B 50/33 (2016.02); *A61B 2050/0088* (2016.02); *A61B 2050/3007* (2016.02); *A61B 2050/314* (2016.02); *A61B 2050/316* (2016.02)

(58) Field of Classification Search
  CPC ......... A61B 50/39; A61B 46/00; A61B 46/10; A61B 46/20; A61B 46/23; A61B 46/30; A47G 11/00; A47G 11/003; A47G 11/004; A47G 11/006
  USPC ............................ 128/849, 853, 854; 53/468
  See application file for complete search history.

(56) References Cited

U.S. PATENT DOCUMENTS

| | | | |
|---|---|---|---|
| 3,981,398 | A | 9/1976 | Boshoff |
| 4,046,254 | A | 9/1977 | Kramer |
| 4,153,160 | A | 5/1979 | Leigh |
| 4,523,679 | A | 6/1985 | Paikoff et al. |
| 4,730,729 | A | 3/1988 | Monch |
| 4,780,940 | A | 11/1988 | Jay |
| 4,790,051 | A | 12/1988 | Knight |
| 4,798,292 | A | 1/1989 | Hauze |
| 4,927,073 | A | 5/1990 | Esposito |
| 5,031,768 | A | 7/1991 | Fischer |
| 5,170,804 | A | 12/1992 | Glassman |
| 5,356,006 | A | 10/1994 | Alpern et al. |
| 6,004,034 | A | 12/1999 | Salam |
| 6,405,863 | B1 | 6/2002 | Dhindsa |
| D480,816 | S | 10/2003 | McMichael et al. |
| 6,907,992 | B2 | 6/2005 | McMichael et al. |
| 6,910,581 | B2 | 6/2005 | McMichael et al. |
| 7,293,654 | B1 | 11/2007 | Wilson et al. |
| 7,337,511 | B2 * | 3/2008 | Yu .......................... A62B 31/00 383/100 |
| 7,401,703 | B2 | 7/2008 | McMichael et al. |
| 7,604,007 | B1 | 10/2009 | Wooley |
| 8,555,892 | B2 * | 10/2013 | Traub ..................... A61B 46/10 206/440 |
| 8,794,833 | B2 | 8/2014 | Runyon et al. |
| 8,894,281 | B2 | 11/2014 | Town et al. |
| 8,894,282 | B2 | 11/2014 | Town et al. |
| 9,072,543 | B2 | 7/2015 | Miller et al. |
| 2001/0045367 | A1 | 11/2001 | Bisbal et al. |
| 2003/0121811 | A1 | 7/2003 | Roshdy |
| 2003/0145443 | A1 | 8/2003 | Lee |
| 2004/0231029 | A1 * | 11/2004 | Kouri ................. A41D 19/0075 2/164 |
| 2005/0033430 | A1 | 2/2005 | Powers et al. |
| 2005/0236940 | A1 | 10/2005 | Rockoff |
| 2006/0289573 | A1 | 12/2006 | Mantuano, Jr. et al. |
| 2007/0009185 | A1 | 1/2007 | Lee |
| 2007/0127852 | A1 | 6/2007 | Town et al. |
| 2008/0031550 | A1 | 2/2008 | Town et al. |
| 2009/0007402 | A1 | 1/2009 | Carroll et al. |
| 2009/0080811 | A1 | 3/2009 | Stefanek et al. |
| 2009/0154844 | A1 | 6/2009 | Greenberg |
| 2010/0054634 | A1 | 3/2010 | Runyon et al. |
| 2010/0263178 | A1 | 10/2010 | Jensen et al. |
| 2012/0145589 | A1 | 6/2012 | Macinnes et al. |
| 2013/0269713 | A1 | 10/2013 | Bui et al. |
| 2014/0021087 | A1 | 1/2014 | Adler et al. |
| 2014/0082836 | A1 | 3/2014 | Patrick et al. |
| 2015/0096475 | A1 | 4/2015 | Lee |
| 2016/0101009 | A1 * | 4/2016 | Newell ................. A61G 17/041 29/455.1 |
| 2017/0281815 | A1 | 10/2017 | Hinora |

\* cited by examiner

BIOLOGICAL CONTAINMENT AND TRANSPORT CARRIERS AND METHODS THEREOF

CROSS-REFERENCE TO RELATED APPLICATIONS

This application is a continuation of U.S. application Ser. No. 17/136,692 filed on Dec. 29, 2020, which is a continuation of U.S. application Ser. No. 15/017,108 filed on Feb. 5, 2016, which claims the benefit of U.S. Provisional Application No. 62/150,739 filed on Apr. 21, 2015, the disclosures of which are hereby incorporated by reference herein in their entirety.

FIELD OF INVENTION

The present general inventive concept relates generally to biological transport carriers, and more particularly to biological containment and transport carriers for use with setup tables in operating rooms, and methods for using the same.

BACKGROUND

During many medical procedures, numerous amounts of instruments and tools are used by health care workers to perform various invasive surgical procedures. Instruments and tools that are opened in a surgical suite, whether used during the procedure or not, must be thoroughly decontaminated prior to disinfection and/or sterilization.

The decontamination procedure, which is time consuming and costly, typically begins during the surgical procedure by using a sterile water-moistened sponge to remove blood and other debris from the instruments and to prevent biological material from drying on the instruments.

Typically, a setup table, also referred to herein as a back table setup 10, is used to assist health care workers in separating and sorting the contaminated instruments 14 at the point of use (e.g., the surgical suite). (See FIG. 1) The health care workers may load trays 12 filled with the contaminated instruments 14 on upper and lower shelves 16 and 18 of the back table setup 10. However, since the back table setups 10 require the health care workers to frequently bend down and reach in between the contaminated instruments 14 and also provide limited visibility to load and unload instruments 14, these back table set-ups 10 often put a considerable amount of burden, stress, and risk of infection on the health care workers.

Figure 1:
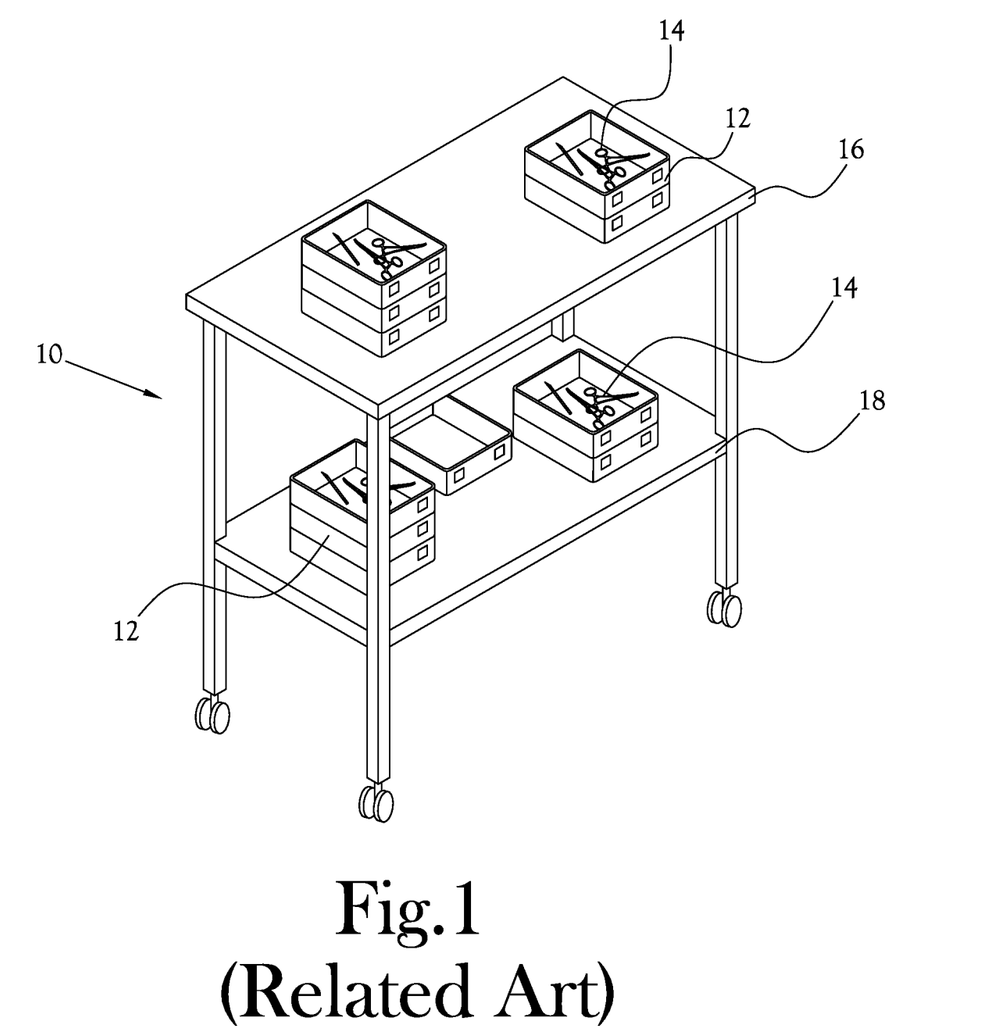
FIG. 1 is a front perspective view of a conventional back table setup cart.

The contaminated instruments 14 and back table setup 10 must then be transported to specific decontamination areas ("SPD") within a facility to be decontaminated prior to re-use. The contaminated equipment may be transported on the back table setup 10 or may be transferred onto specifically designed transport carts. However, due to the costs associated with obtaining, decontaminating, and maintaining back table setups 10 and these transport carts, many medical facilities maintain a limited number of back table setups 10 and transport carts which are repeatedly decontaminated and re-used.

Consequently, there is a need for a disposable bio containment apparatus and method for containing contaminated instruments at a point of use which reduces cross-contamination during transport, reduces risk of infection exposure to health care workers, and also reduces costs for medical facilities.

BRIEF SUMMARY

Example embodiments of the present general inventive concept provide a biological containment and transport carrier apparatus including for use with a table in an operating room to store surgical equipment, including a base layer having an inner surface and an opposing outer surface, a top layer having an inner surface and an opposing outer surface, a perimeter of the top layer being coupled to a perimeter of the base layer to form a sealed bag, and a zipper formed within the top layer configured to open and close an insertion flap to provide access to a cavity formed between the base layer and the top layer such that when the zipper is open, a portion of the top layer extending around the zipper is configured to fold inside out over a top surface of the table and to extend below the top surface to secure the base layer to the top surface of the table.

The base layer and the top layer can include a length and a width defined by a length and width of the top surface of the table.

The inside out folded portion of the top layer can be configured to form a sterile drape portion extending below a bottom surface of the table.

The sterile drape portion can extend at least two inches below the bottom surface of the table.

The base layer and the top layer may be constructed from a puncture resistant material.

The base layer and the top layer may be constructed from a leak resistant material.

The base layer and the top layer may be constructed from a material having a thickness between about 0.2 millimeters to 10 millimeters.

The base layer and the top layer may be constructed from a material configured to be an antimicrobial barrier from the table.

The cavity formed between the base layer and the top layer may be sealed off from an external environment when the zipper is closed.

The cavity formed between the base layer and the top layer may be open to an external environment when the insertion flap is in an open state.

The sealed bag formed between the base layer and the top layer may be leak proof when the zipper is closed.

Example embodiments of the present general inventive concept can also provide a method of containing and transporting bio-contaminated instruments when storing surgical instruments on a table in an operating room, including obtaining a biological containment and transport carrier including a base layer having an inner surface and an outer surface, a top layer having an inner surface and an outer surface, the top layer coupled to the base layer, and a zipper formed in a central portion of the top layer, the zipper can be configured to open and close an insertion flap formed by the top layer when the zipper is open and closed, respectively, wherein the inner surface of the base layer is configured to lie flat on a surface of a table and wherein end and corner portions of the top layer are configured to fold inside out to secure the base layer to the surface of the table, placing the outer surface of the base layer on the surface of the table, opening the insertion flap by using the zipper, folding the portions of the top layer around the zipper inside out to secure the base layer to the surface of the table, placing bio-contaminated instruments within an opening of the top layer defined by the insertion flap, unfolding the inside out portions of the top layer around the zipper, and closing the insertion flap by using the zipper to contain the bio-contaminated instruments between the base layer and the top layer.

Additional features and embodiments of the present general inventive concept will be apparent from the following detailed description, drawings, and claims.

BRIEF DESCRIPTION OF THE FIGURES

The following example embodiments are representative of example techniques and structures designed to carry out the objects of the present general inventive concept, but the present general inventive concept is not limited to these example embodiments. In the accompanying drawings and illustrations, the sizes and relative sizes, shapes, and qualities of lines, entities, and regions may be exaggerated for clarity. A wide variety of additional embodiments will be more readily understood and appreciated through the following detailed description of the example embodiments, with reference to the accompanying drawings in which.

DETAILED DESCRIPTION

Reference will now be made to the example embodiments of the present general inventive concept, examples of which are illustrated in the accompanying drawings and illustrations. The example embodiments are described herein in order to explain the present general inventive concept by referring to the figures.

The following detailed description is provided to assist the reader in gaining a comprehensive understanding of the structures and fabrication techniques described herein. Accordingly, various changes, modification, and equivalents of the structures and fabrication techniques described herein will be suggested to those of ordinary skill in the art. The progression of fabrication operations described are merely examples, however, and the sequence type of operations is not limited to that set forth herein and may be changed as is known in the art, with the exception of operations necessarily occurring in a certain order. Also, description of well-known functions and constructions may be simplified and/or omitted for increased clarity and conciseness.

Numerous variations, modifications, and additional embodiments are possible, and accordingly, all such variations, modifications, and embodiments are to be regarded as being within the spirit and scope of the present general inventive concept. For example, regardless of the content of any portion of this application, unless clearly specified to the contrary, there is no requirement for the inclusion in any claim herein or of any application claiming priority hereto of any particular described or illustrated activity or element, any particular sequence of such activities, or any particular interrelationship of such elements. Moreover, any activity can be repeated, any activity can be performed by multiple entities, and/or any element can be duplicated.

It is noted that the simplified diagrams and drawings included in the present application do not illustrate all the various connections and assemblies of the various components, however, those skilled in the art will understand how to implement such connections and assemblies, based on the illustrated components, figures, and descriptions provided herein. Numerous variations, modification, and additional embodiments are possible, and, accordingly, all such variations, modifications, and embodiments are to be regarded as being within the spirit and scope of the present general inventive concept.

The present general inventive concept provides a disposable bio-containment instrument transport bag which reduces cross-contamination and controls bio-burden exposure when transporting instruments used or exposed during medical procedures from a point of use (e.g., a surgical suite) to a decontamination area (e.g. a sterile processing department). The bio-containment instrument transport bag may be constructed from a heavy duty puncture and leak resistant material that further acts as an anti-microbial barrier between a table and the contaminated medical instruments. The bio-containment instrument transport bag may further control exposure of bio-aerosols from the contaminated medical instruments stored therein when being transported from the surgical suite to a decontamination area through various semi sterile areas within the facility.

Figure 2:
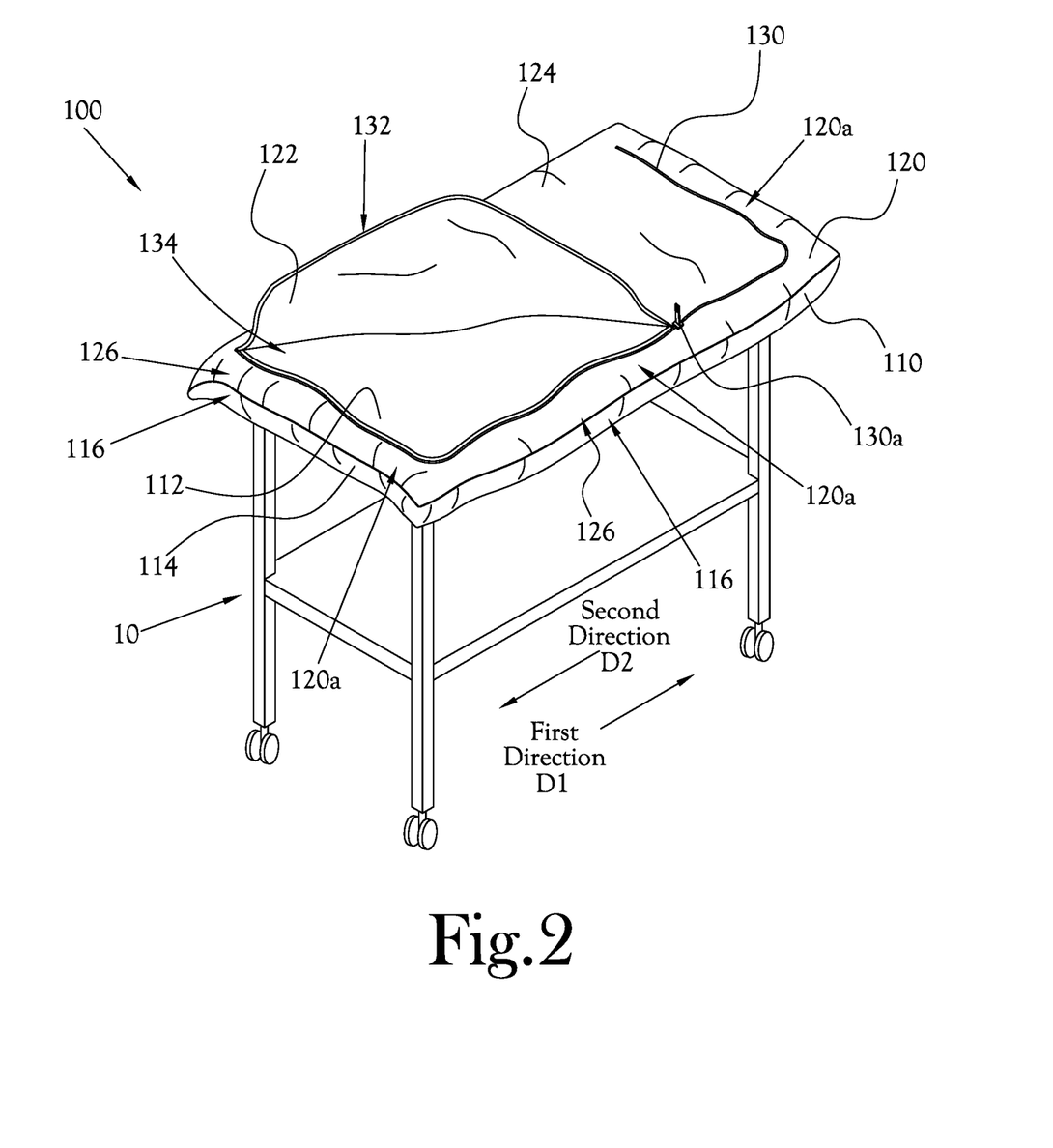
FIG. 2 is a front perspective view of a biological containment and transport carrier according to an example embodiment of the present general inventive concept, wherein an insertion flap is in a partially open state.

FIG. 2 is a front perspective view of a biological containment and transport carrier 100 according to an example embodiment of the present general inventive concept, wherein an insertion flap is in a partially open state. Referring to FIG. 2, the biological containment and transport carrier 100 may include a base layer 110 having an inner surface 112 and an opposing outer surface 114, a top layer 120 having an inner surface 122 and an opposing outer surface 124, and a zipper 130 formed which can be formed in a u-shape along edges (e.g., along three sides) and corners of the top layer 120.

In the present example embodiment, a perimeter 116 of the base layer 110 may be coupled and sealed to a perimeter 126 of the top layer 120 to form a sealed bag. However, the present general inventive concept is not limited thereto. That is, in alternative example embodiments, a portion of the perimeter 116 of the base layer 110 may be coupled and sealed to a portion of the perimeter 126 of the top layer 120 to form the sealed bag.

In the present example embodiment, the zipper 130 may be configured in a u-shape to open and close an insertion flap 132 to provide access to a cavity 134 formed in between the base layer 110 and the top layer 120. That is, the zipper 130 may include a movable zipper member 130a which opens the insertion flap 132 when moved along a first direction D1 and closes the insertion flap 132 when moved along a second direction D2.

Figure 3:
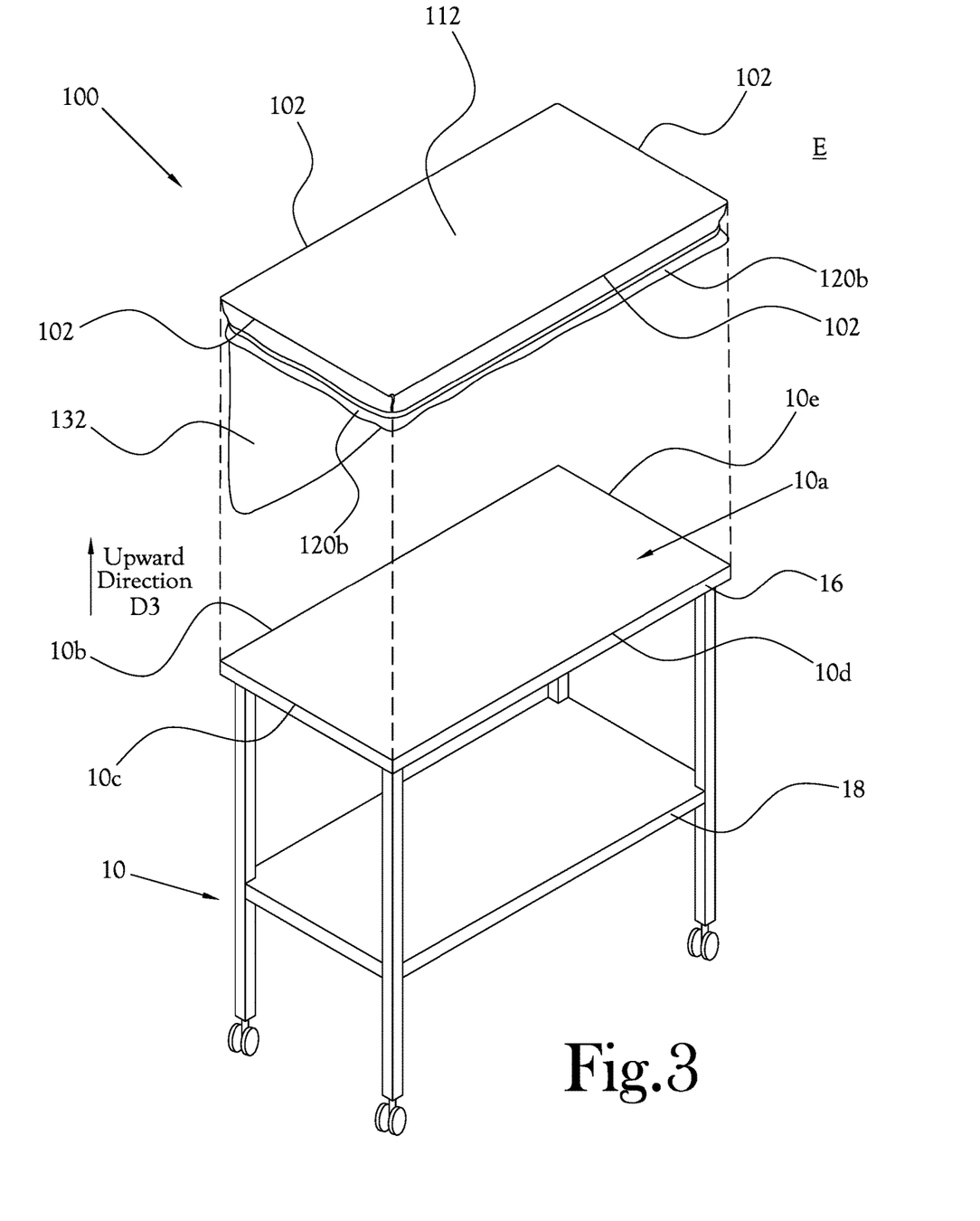
FIG. 3 is an exploded front perspective assembly view of the biological containment and transport carrier illustrated in FIG. 2 and a back table setup.

FIG. 3 is an exploded front perspective assembly view of the biological containment and transport carrier 100 illustrated 100 in FIG. 2 and a back table setup 10. Referring to FIG. 3, the base layer 110 may be coupled to the top layer 120 in such a manner so as to create an inner seam 102 within the cavity 134 formed between the base layer 110 and the top layer 120. The inner seam 102 may be formed around the perimeter 116 of the base layer 110 and may be sized and shaped so as to correspond or match a size and shape of the back table setup 10.

In the present example embodiment, as illustrated in FIGS. 2 and 3, a portion 120a of the top layer 120 surrounding the zipper 130 may be designed and/or configured to fold inside out to thereby secure the base layer 110 to the back table setup 10.

In alternative example embodiments, the base layer 110 and the top layer 120 may be custom designed to include a width dimension (e.g., 44 inches) and a length dimension (e.g., 36 or 68 inches) to correspond or match width and length dimensions of a surface 10a of a certain back table 10. That is, the inner seam 102 formed within the cavity 134 may include a width dimension which corresponds to and matches a width dimension of the surface 10a of the back table 10 and a length dimension which corresponds to and matches a length dimension of the surface 10a of the back table 10. As such, by folding the portion 120a of the top layer 120 inside out around the table 10, the inner surface 112 of the base layer 110 may thereby be securely affixed so that the base layer 110 is parallel and/or flat with respect to the surface 10a of the back table 10.

Figure 4:
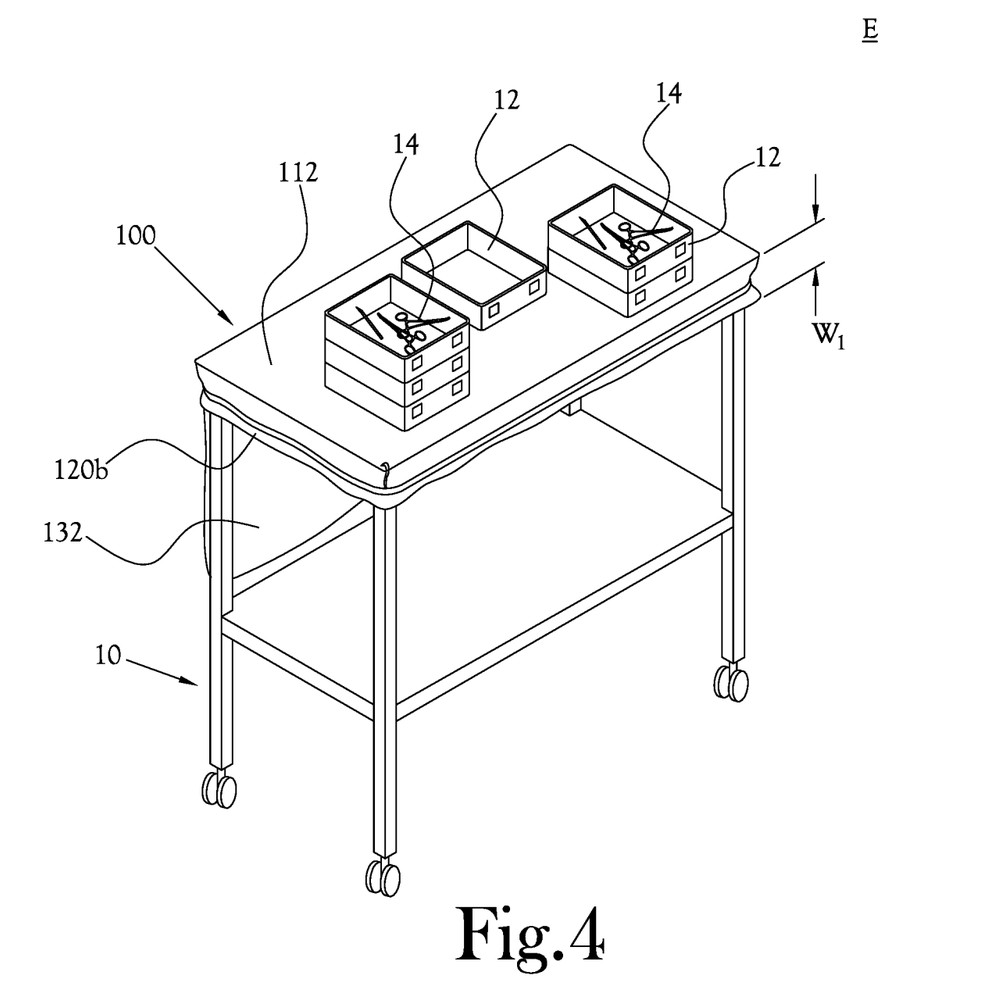
FIG. 4 is a front perspective view of the biological containment and transport carrier illustrated in FIG. 3 secured to the back table setup, wherein the insertion flap is in a fully open state.

FIG. 4 is a front perspective view of the biological containment and transport carrier illustrated 100 in FIG. 3 secured to the back table setup 10, wherein the insertion flap 132 is in a fully open state.

Referring now to FIGS. 2 through 4, in the present example embodiment, a user (e.g., a health care worker) may place the transport carrier 100 onto the surface 10a of the back table 10 so that the outer surface 114 of the base layer 110 faces and contacts the surface 10a of the table 10, and the top layer 120 faces an upward direction.

The user may then slide or move the zipper member 130a along the first direction D1 to open the insertion flap 132. In the present example embodiment, the cavity 134 formed between the base layer 110 and the top layer 120 may be sealed off from the external environment E when the insertion flap 132 is in a closed state and may be exposed to the external environment E when in an open state. The user may then fold open the insertion flap 132 over a side 10b (e.g., a back side) of the back table 10 to expose the cavity 134 formed in between the base layer 110 and top layer 120 to the external environment E.

The user may then fold the portion 120a of the top layer 120 around the zipper 130 inside out over and around all the sides 10b, 10c, 10d, and 10e of the back table 10 to thereby secure the transport carrier 100 to the surface 10a of the back table 10. In addition, the portion 120b of the top layer 110 may be configured and/or designed to secure the insertion flap 132 to the side of the back table 10 when folded inside out.

In the present example embodiment, the inside out folded portion 120b of the top layer 110 may form a sterile drape portion, or margin border, extending around all sides 10b, 10c, 10d, and 10e of the table. The sterile drape portion may extend to a distance W1 below the surface 10a of the back table 10, for example a distance of about 2 inches. However, the present general inventive concept is not limited to any particular distance W1 for the sterile margin created by the inside out folded portion. The inside out folded out portion of the top layer is constructed and designed to create the sterile drape portion when the zipper is open. The structure is dimensioned to substantially match the dimensions of the table such that the when the device is situated on the top surface of the table, the edge and/or corner portions are designed to wrap around one or more outer edges of the table and extend a predetermined distance below the bottom surface of the table to secure the base layer to the table and to provide a sterile margin, or drape portion, around the table, and to provide a custom fit for the table to allow for sterile use in procedure of setup packs with reduced exposure of contaminated surfaces.

For example, during and/or after a medical procedure, users (e.g., health care workers) may easily load medical trays 12 filled with contaminated instruments 14 onto a flat inner surface 112 of the base layer 110, which has been detachably secured to the back table 10.

The biological containment and transport carrier 100 according to the present inventive concept provides complete visibility of the entire surface 10a of the back table 10, thereby reducing the health care workers exposure risk for infection when loading and/or unloading the contaminated instruments 14 into and out of the transport carrier 100. In addition, the transport carrier 100 may further provide a microbacterial barrier between the contaminated instruments 14 and the surface 10a of the back table 10 to reduce a risk of cross-contamination and to allow for sterile use in procedure setup packs. The carrier is designed to specifically meet specifications for surgical instrument transport.

Once the health care workers finish loading the inner surface 112 of the base layer 110 with contaminated instruments 14, the folded portion 120b may then be unfolded from the table 10 to thereby release the base layer 110 from the surface 10a of the table 10.

Figure 5:
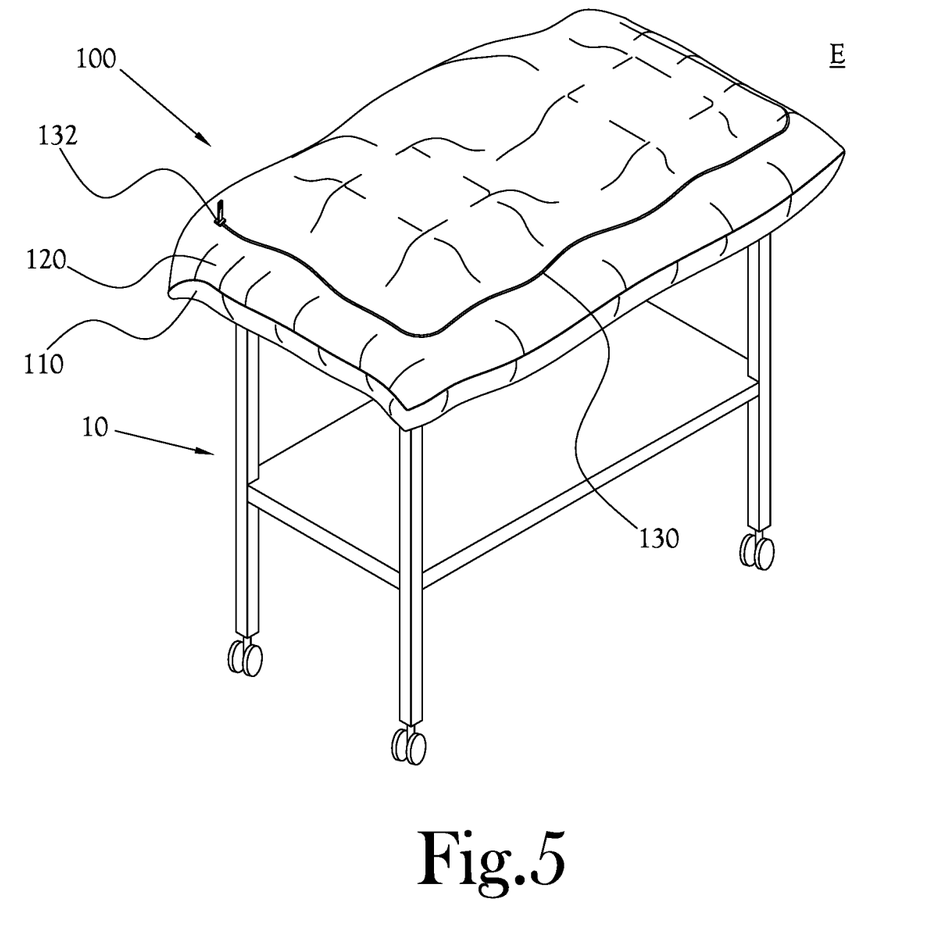
FIG. 5 is a front perspective view of the biological containment and transport carrier illustrated in FIG. 3 filled with contaminated instruments.

FIG. 5 is a front perspective view of the biological containment and transport carrier 100 illustrated in FIG. 3 filled with contaminated instruments 14. Referring to FIG. 5, the health care worker may then fold the insertion flap 132 back over the contaminated instruments 14 and close the insertion flap 132 to contain and/or seal off the contaminated instruments 14 from the external environment E. In the open state, the configuration of the zipper which is designed to extend around at least one side of the length and both end width portions of the carrier permits the top layer to be lifted up and away from a top front edge of the table such a person standing in front of the table can visualize contents of the container or place additional instruments into the container. The zipper can then be closed to seal the contaminated instruments therein, without requiring squatting or bending of the person. In the present example embodiment, the sealed bag formed between the base layer 110 and the top layer 120 is leak proof when the insertion flap 132 is in the closed state. The bag may be provided and packaged for use in an unsterile form, or it may be added to sterile procedure packs for use as a table cover that converts to a transport bag.

In alternative example embodiments, the zipper 130 may include an elastic portion (not illustrated) to further assist in securing the base layer 110 to the table 10 when folded inside out around the edges of the back table 10.

In alternative example embodiments, the base layer 110 and the top layer 120 may be constructed from a heavy duty puncture resistant and/or leak resistant material. The material may have a thickness between about 0.2 millimeters to 10 millimeters, which has been found to provide sufficient leak and/or puncture resistance properties in view of the specific types of instruments that may be stored therein, and may include antimicrobial properties so as to create a microbacterial barrier between the surface 10a of the table 10 and objects placed on the base layer 110. This addresses sharp instrument protocols and guidelines for sharp instruments. However, the present general inventive concept is not limited to any particular thickness or material. For example, in some example embodiments, the base layer 110 and the top layer 120 may be constructed from a variety of single or multi-layered barrier fabrics including non-woven polypropylene and/or various other polymeric materials.

Figure 6:
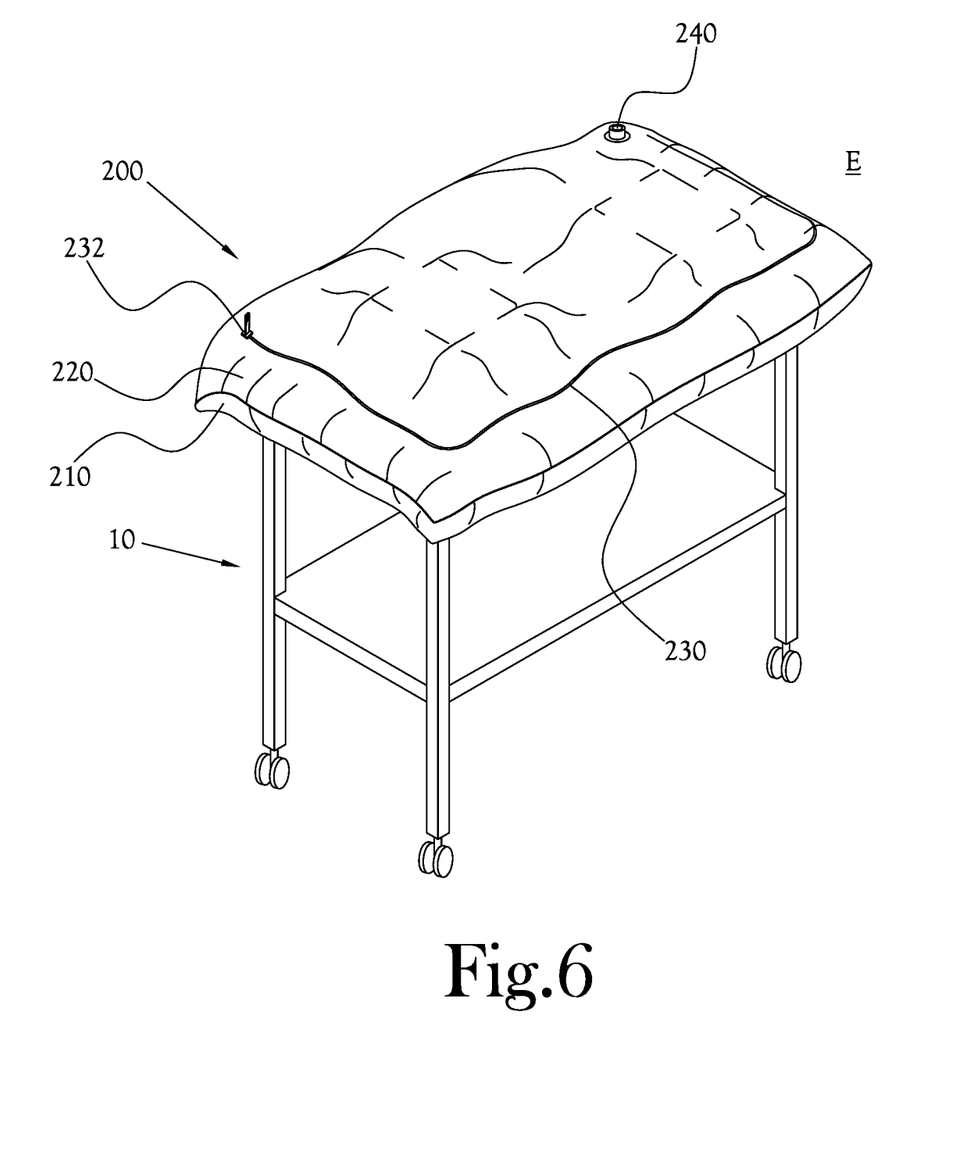
FIG. 6 is a front perspective view of a biological containment and transport carrier according to another example embodiment of the present general inventive concept.

FIG. 6 is a front perspective view of a biological containment and transport carrier 200 according to another example embodiment of the present general inventive concept. Referring to FIG. 6, the biological containment and transport carrier 200 according to the present example embodiment includes the elements and/or features as described in the previous example embodiments. That is, the biological containment and transport carrier 200 may include a base layer 210 having an inner surface 212 and an opposing outer surface 214, a top layer 220 having an inner surface 222 and an opposing outer surface 224, and a u-shaped zipper 230 formed along edges (e.g., along three sides) of the top layer 220. In addition, the biological containment and transport carrier 200 according to the present example embodiment may further include a vacuum port 240 formed through the top layer 220 which may be used to vacuum seal the transport carrier 200. A vacuuming device (not illustrated) may be detachably coupled to the vacuum port 240 to safely remove air, bio-burden, and/or bio-aerosols within the cavity 234 formed between the base layer 210 and the top layer 220, when the insertion flap 232 is in a closed state. In the present example embodiment, the vacuum port 240 allows the health care workers to vacuum seal the biological containment and transport carrier 200 to reduce a risk of cross-contamination when transporting the transport carrier 200 from the point of use to a specific decontamination area.

Figure 7:
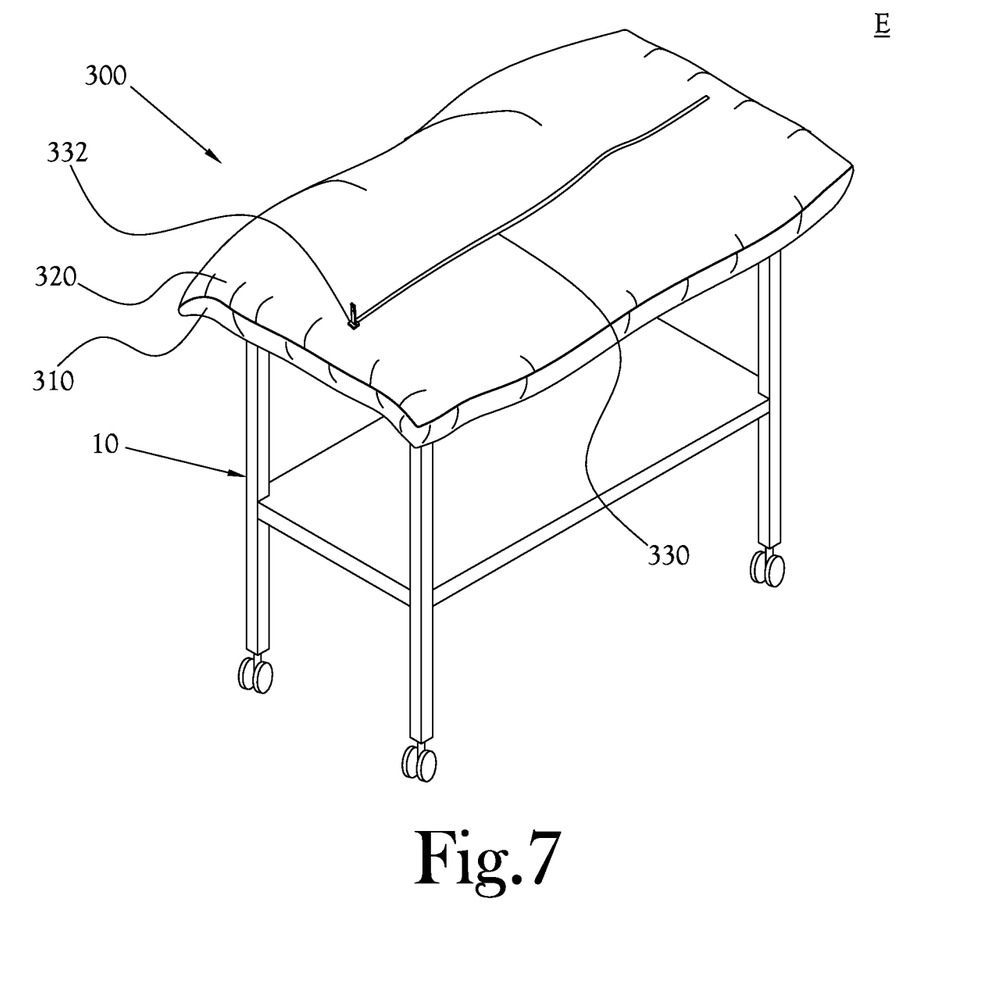
FIG. 7 is a front perspective view of a biological containment and transport carrier according to another example embodiment of the present general inventive concept.

FIG. 7 is a front perspective view of a biological containment and transport carrier 300 according to another example embodiment of the present general inventive concept. Referring to FIG. 7, the biological containment and transport carrier 300 according to the present example embodiment may include the features and/or elements as described in the previous example embodiments. The biological containment and transport carrier 300 may include a base layer 310 having an inner surface 312 and an opposing outer surface 314, a top layer 320 having an inner surface 322 and an opposing outer surface 324, and a zipper 330 formed along central portion of the top layer 320.

The biological containment and transport carrier according to the present general inventive concept provides a disposable bio-containment instrument transport bag which reduces cross-contamination and controls bio-burden exposure when transporting contaminated instruments from a point of use (e.g., a surgical suite) to a decontamination area (e.g. a sterile processing department). The biological containment and transport carrier provides a barrier between the contaminated instruments and reduces cross contamination and controls bio-burden and bio-aersols during post-operative transport of the contaminated instruments through semi sterile areas from the point of use to the specific decontamination areas.

The biological containment and transport carrier provides an airtight and/or water proof cavity in which the contaminated instruments are kept moist for ease of cleaning even hours after the medical procedures. The biological containment and transport carrier may further be constructed of a disposable material which allows health care workers to easily load, transport, and unload contaminated instruments after medical procedures and then dispose the biological containment and transport carrier to reduce costs associated with maintaining and cleaning and decontaminating wash cycles of conventional back table setups. Embodiments of the present general inventive concept reduce expenses and labor associated with cart maintenance and cart washing cycles and expedite sterile instrument reprocessing. Operating room turnover time is reduced.

While the present general inventive concept has been illustrated by description of several example embodiments, and while the illustrative embodiments have been described in detail, it is not the intention of the applicant to restrict or in any way limit the scope of the general inventive concept to such descriptions and illustrations. Instead, the descriptions, drawings, and claims herein are to be regarded as illustrative in nature, and not as restrictive, and additional embodiments will readily appear to those skilled in the art upon reading the above description and drawings. Additional modifications will readily appear to those skilled in the art. Accordingly, departures may be made from such details without departing from the spirit or scope of applicant's general inventive concept.

What is claimed is:

1. A biological containment and transport carrier apparatus for use with an equipment table in an operating room, comprising:
   a base layer having an inner surface and an opposing outer surface;
   a top layer having an inner surface and an opposing outer surface, a perimeter of the top layer being coupled to a perimeter of the base layer to form a sealed bag, wherein the base layer and the top layer define an inner cavity, wherein the base layer and the top layer further define an outer surface of the apparatus;
   an inner seam portion formed between the base layer and the top layer, the inner seam portion having a length and width dimension configured to respectively match a length and a width dimension of a top surface of an equipment table in an operating room; and
   a zipper formed within the top layer, wherein the zipper includes a movable zipper member configured to open an insertion flap of the top layer when moved along a first direction so as to provide access to the inner seam portion and the inner cavity and to close the insertion flap when moved along a second direction that is opposite the first direction such that, when the zipper is open, at least a portion of the inner seam portion is configured to fold inside out over a top surface of the table and wrap around outer edges of the length and width dimension of the top surface of the equipment table and mate with the length and width dimension of the top surface of the equipment table so as to secure the base layer to the equipment table such that the inner surface of the top layer extends perpendicularly below the top surface of the equipment table to create a sterile drape portion surrounding the perimeter of the equipment table,
   wherein, when the zipper is closed, the inner cavity of the entire biological containment and transport carrier apparatus is liquid-proof.

2. The biological containment and transport carrier apparatus of claim 1, wherein the base layer and the top layer are constructed from a material configured to be an antimicrobial barrier from the table.

3. The biological containment and transport carrier apparatus of claim 2, wherein the base layer and the top layer are constructed from a puncture resistant material.

4. The biological containment and transport carrier apparatus of claim 3, wherein the base layer and the top layer are constructed from a leak resistant material.

5. The biological containment and transport carrier apparatus of claim 1, further comprising a vacuum port formed through the top layer, wherein the vacuum port is configured to vacuum seal the biological containment and transport carrier apparatus from external environment.

6. The biological containment and transport carrier apparatus of claim 1, wherein, when the zipper is closed, the entire biological containment and transport carrier apparatus forms an airtight cavity.

7. A method of containing and transporting bio-contaminated instruments when storing surgical instruments on an equipment table in an operating room, comprising:
    covering a top surface of an equipment table in an operating room with a biological containment and transport carrier, the biological containment and transport carrier comprising:
        a base layer having an inner surface and an opposing outer surface;
        a top layer having an inner surface and an opposing outer surface, a perimeter of the top layer being coupled to a perimeter of the base layer to form a sealed bag, wherein the base layer and the top layer define an inner cavity, wherein the base layer and the top layer further define an outer surface of the apparatus;
        an inner seam portion formed between the base layer and the top layer, the inner seam portion having a length and width dimension configured to respectively match a length and a width dimension of a top surface of an equipment table in an operating room; and
        a zipper formed within the top layer, wherein the zipper includes a movable zipper member configured to open an insertion flap of the top layer when moved along a first direction so as to provide access to the inner seam portion and the inner cavity and to close the insertion flap when moved along a second direction that is opposite the first direction such that, when the zipper is open, at least a portion of the inner seam portion is configured to fold inside out over a top surface of the table and wrap around outer edges of the length and width dimension of the top surface of the equipment table and mate with the length and width dimension of the top surface of the equipment table so as to secure the base layer to the equipment table such that the inner surface of the top layer extends perpendicularly below the top surface of the equipment table to create a sterile drape portion surrounding the perimeter of the equipment table,
    wherein, when the zipper is closed, the inner cavity of the entire biological containment and transport carrier is liquid-proof.

8. The method of claim 7, further comprising:
opening the insertion flap by opening the zipper;
folding the portion of the top layer inside out over the top surface of the equipment table such that the inner surface of the base layer lies flat on the top surface of the equipment table and the inner seam portion secures the base layer to the top surface of the equipment table;
placing bio-contaminated instruments onto the inner surface of the base layer;
releasing the inner seam portion from the top surface of the equipment table by unfolding the portions of the top layer outside in; and
closing the insertion flap to contain the bio-contaminated instruments between the base layer and the top layer by closing the zipper.

9. The method of claim 7, wherein, when the zipper is closed, the entire biological containment and transport carrier forms an airtight cavity.

* * * * *